United States Patent
Zou et al.

(10) Patent No.: US 10,137,443 B2
(45) Date of Patent: Nov. 27, 2018

(54) COMPOSITE CATALYST FOR THE PHOTOCATALYTIC ISOMERISATION OF NORBORNADIENE TO PREPARE QUADRICYCLANE AND PROCESS FOR MAKING THE CATALYST

(71) Applicant: TIANJIN UNIVERSITY, Tianjin (CN)

(72) Inventors: Jijun Zou, Tianjin (CN); Xiangwen Zhang, Tianjin (CN); Li Wang, Tianjin (CN); Qingfa Wang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 14/648,896

(22) PCT Filed: May 23, 2014

(86) PCT No.: PCT/CN2014/078211
§ 371 (c)(1),
(2) Date: Jun. 1, 2015

(87) PCT Pub. No.: WO2015/120669
PCT Pub. Date: Aug. 20, 2015

(65) Prior Publication Data
US 2016/0339415 A1    Nov. 24, 2016

(30) Foreign Application Priority Data
Feb. 17, 2014    (CN) .......................... 2014 1 0052298

(51) Int. Cl.
*B01J 31/02*    (2006.01)
*C07C 5/22*    (2006.01)
(Continued)

(52) U.S. Cl.
CPC ......... *B01J 31/0208* (2013.01); *B01J 35/004* (2013.01); *B01J 37/009* (2013.01);
(Continued)

(58) Field of Classification Search
None
See application file for complete search history.

(56) References Cited

U.S. PATENT DOCUMENTS

2008/0057420 A1*    3/2008    Inagaki .................. C09K 11/06
430/56
2010/0135939 A1*    6/2010    Lehmann ................. A61K 8/11
424/60

FOREIGN PATENT DOCUMENTS

CN    102860926 A    *    1/2013

OTHER PUBLICATIONS

Da Silva et al, Photochemistry of benzophenone on Ti-MCM-41 surfaces, 2006, Microporous and Mesoporous Materials, 89, 143-149.*

(Continued)

*Primary Examiner* — Melvin C. Mayes
*Assistant Examiner* — Stefanie J Cohen
(74) *Attorney, Agent, or Firm* — Gokalp Bayramoglu

(57) ABSTRACT

The present invention discloses a composite catalyst for the photocatalytic isomerization of norbornadiene to prepare quadricyclane, comprising: a solid photocatalyst, selected from the group consisting of $TiO_2$, Ti-MCM-41, Ti-SBA-15, ZnO, $WO_3$, $Ta_2O_5$ or $SrTiO_3$; and an organic photo-sensitizer loaded on the surface or in the channel of said solid photocatalyst, selected from benzophenone, acetophenone, Michler's Ketone, tetraethyl Michler's Ketone, and diethyl Michler's Ketone, where the organic photo-sensitizer is present in the solid photocatalyst in an amount of 0.5% to 20% by weight. The catalyst of the invention can catalyze a target reaction under the condition that no solvent is used, and the yield of the target product quadricyclane is higher. Furthermore, the catalyst of the invention has a stable (Continued)

activity, and it can be recycled. The invention further discloses a process for preparing the composite catalyst.

1 Claim, 3 Drawing Sheets

(51) Int. Cl.
B01J 35/00 (2006.01)
B01J 37/00 (2006.01)
B01J 37/04 (2006.01)

(52) U.S. Cl.
CPC .............. B01J 37/04 (2013.01); C07C 5/222 (2013.01); C07C 5/2213 (2013.01); C07C 5/2266 (2013.01); C07C 2521/06 (2013.01); C07C 2521/08 (2013.01); C07C 2523/02 (2013.01); C07C 2523/06 (2013.01); C07C 2523/20 (2013.01); C07C 2523/30 (2013.01); C07C 2529/70 (2013.01); C07C 2531/02 (2013.01); C07C 2603/86 (2017.05)

(56) References Cited

OTHER PUBLICATIONS

Wang et al, Photocatalytic Activity of a Hierarchically Macro/Mesoporous Titania, 2005, Langmuir, 21, pp. 2552-2559.*

Babkov et al, Specific Intermolecular Interactions in a Heterogeneous System Benzophenone-Titanium Dioxide, 2006, Journal of Structural Chemistry. vol. 47, No. 5, pp. 946-951.*

Ii et al, characterization and photocatalytic properties of titanium-containing mesoporous sba-15, ind. eng. chem. res. 45 (10) pp. 3359-3573 (Year: 2006).*

English translation of CN102860926, Jan. 9, 2013 (Year: 2013).*

* cited by examiner

COMPOSITE CATALYST FOR THE PHOTOCATALYTIC ISOMERISATION OF NORBORNADIENE TO PREPARE QUADRICYCLANE AND PROCESS FOR MAKING THE CATALYST

CROSS-REFERENCE TO RELATED APPLICATIONS

This application is a 371 of PCT/CN2014/078211 filed May 23, 2014 which claims benefit of CN 201410052298.0 filed on Feb. 17, 2014, both of which are incorporated herein by reference in their entireties.

FIELD OF THE INVENTION

The invention is in the field of the catalyst preparation.

BACKGROUND OF THE INVENTION

The quadricyclane, being an important high-energy aerospace fuel, has a density of up to 0.98 g·cm$^{-3}$, and the ice point lower than −40° C., and the substance can be used in propelling systems of aerospace vehicles, for example, such as rockets, guided missiles, satellites, and space crafts. As compared with kerosene fuels, the quadricyclane has the high-energy advantage, and as compared with hydrazine fuels, it has the advantage of the high safety.

The quadricyclane may be synthesized via a photochemical process, that is, norbornadiene, as the starting material, is used to form the quadricyclane via the intermolecular adduct reaction of norbornadiene with ultraviolet radiations and in the presence of an organic photo-sensitizer or a solid photocatalyst as the catalyst for the reaction. The catalyst is an essential factor for determining the reaction velocity.

The photocatalytic isomerization of norbornadiene to synthesize the quadricyclane uses two kinds of catalysts, one kind being an organic photo-sensitizer, and another kind being a solid photocatalyst.

The organic photo-sensitizer may be dissolved in the reaction solution, and thus it can also be called as a homogenous phase photo-sensitizer. Commonly-used organic photo-sensitizers are organic ketone-based photo-sensitizers, e.g., benzophenone, acetophenone, Michler's Ketone, tetraethyl Michler's Ketone, and diethyl Michler's Ketone.

In the U.S. Pat. No. 5,076,813, a solution containing 110 g norbornadiene and 0.1 g Michler's Ketone is irradiated with a 150 W high-pressure mercury lamp. After the reaction is effected for 37 hours, the resultant conversion rate is 99%, and the selectivity of the quadricyclane is 99%.

In patent publication US2004/0054244 A1, solutions containing 5 ml norbornadiene and 0.32% Michler's Ketone or 0.75% ethyl Michler's Ketone are respectively irradiated with a 400 W high-pressure mercury lamp for 16 hours, the resultant conversion rates are 53.7% and 65.8% respectively.

The solid photocatalyst is not dissolved in the reaction solution, and thus it is also called as a non-homogenous phase photocatalyst. The applicant of the present patent early reports a V-Ti-MCM-41 solid photocatalyst (Applied Catalysis B (2010) 439-445), and a solution containing 5 ml norbornadiene, 0.1 g the catalyst and 500 ml xylene is irradiated with a 400 W high-pressure mercury lamp for 4 hours, the resultant conversion rate being 90%.

However, existing catalysts have various disadvantages. Because the organic photo-sensitizer can be dissolved in reaction solution, its separation and recovery from reaction product and reactants which are not sufficiently reacted will become a problem. Furthermore, the organic photo-sensitizer has a low activity. Thus, in the case that no solvent is added, the reaction time should be 20 hours or above, and in the case that a dilution solvent is added, the reaction time may be decreased to less 10 hours. However, because of the dilution action of the solvent, the treating amount of reactants per unit time is low, and thus the need of a large-scale preparation is hard to meet.

Although the use of a solid photocatalyst can solve the problem of separation and recovery of the catalyst from the reaction system, the reaction should be carried out in the presence of large quantities of solvents. Thus, the treating amount of reactants in unit time is limit, thereby restricting the application of the solid photocatalyst.

Hence, a novel catalyst having a higher activity for the photo-catalytic isomerisation of norbornadiene to prepare quadricyclane is desired. The catalyst is desired, in the case that no solvent is added, to realize a quadricyclane yield of higher than 90% within 10 hour reaction time, and the catalyst should have a stable activity and be easily separated and recovered.

The present invention is aimed to solve the above problems.

SUMMARY OF THE INVENTION

Figure 1:
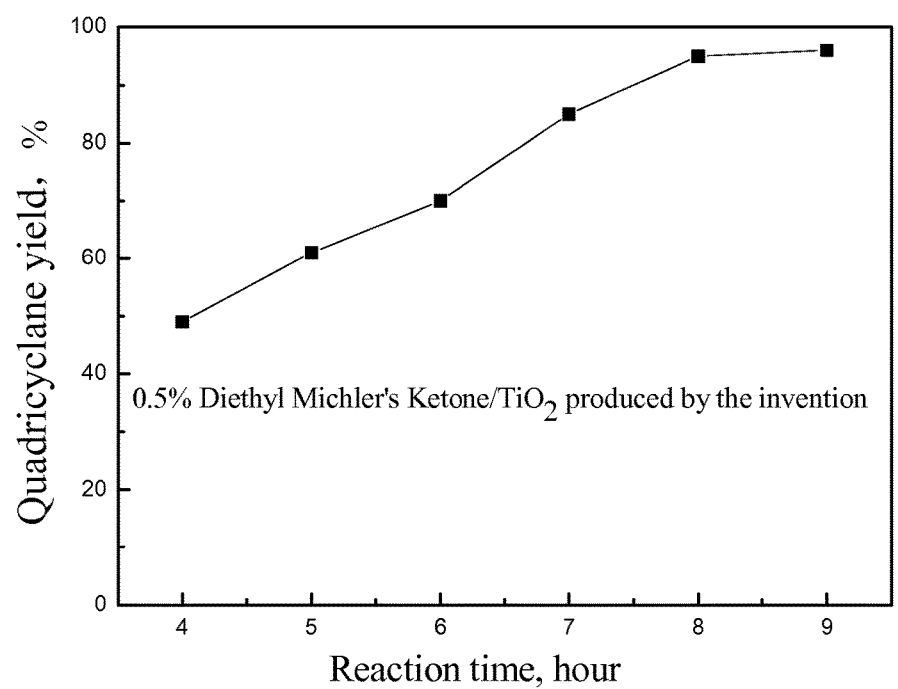
FIG. 1 is a diagram which describes the variation of the quadricyclane yield with the time in the presence of the catalyst of the invention.

A first aspect of the invention relates to a composite catalyst for photocatalystic, isomerisation of norbornadiene to prepare quadricyclane, comprising: A solid photocatalyst, selected from the group consisting of $TiO_2$, Ti-MCM-41, Ti-SBA-15, ZnO, $WO_3$, $Ta_2O_5$ or $SrTiO_3$; and an organic photo-sensitizer loaded on the surface or in the channel of said solid photocatalyst, selected from benzophenone, acetophenone, Michler's Ketone, tetraethyl Michler's Ketone, or diethyl Michler's Ketone; and where the organic photo-sensitizer is present in the solid photocatalyst in an amount of 0.5% to 20% by weight.

In one preferred embodiment of the first aspect, said organic photo-sensitizer is bound to hydroxyl groups on the surface of the solid photocatalyst.

The second aspect of the present invention relates to a process of preparing a composite catalyst for the photocatalytic isomerisation of norbornadiene to prepare quadricyclane, comprising the steps: (a) mixing a solution obtained by dissolving an organic photo-sensitizer in an organic solvent with a dried solid photocatalyst under sufficient stirring, wherein the weight ratio of the organic photo-sensitizer to the solid photocatalyst ranging from 0.5% to 20%, so that the organic photo-sensitizer is adsorbed onto the surface of the solid photocatalyst, wherein the solid photocatalyst is selected from $TiO_2$, Ti-MCM-41, Ti-SBA-15, ZnO, $WO_3$, $Ta_2O_5$ or $SrTiO_3$; and the organic photo-sensitizer is selected from benzophenone, acetophenone, Michler's Ketone, tetraethyl Michler's Ketone, or diethyl Michler's Ketone; and (b) filtering off redundant solution and vacuum drying the solid photocatalyst which adsorbed the organic photo-sensitizer.

In the first and second aspects of the invention, the composite catalyst comprises a solid photocatalyst which is selected from $TiO_2$, Ti-MCM-41, Ti-SBA-15, ZnO, $WO_3$, $Ta_2O_5$ or $SrTiO_3$, and an organic photo-sensitizer loaded on the surface or channels of the solid photocatalyst which is selected from benzophenone, acetophenone, Michler's Ketone, tetraethyl Michler's Ketone, and diethyl Michler's Ketone, wherein the organic photo-sensitizer is present in an amount of 0.5 to 20% by weight of the solid photocatalyst.

The catalyst of the invention is a composite catalyst, i.e., an organic photo-sensitizer is bound to a solid photocatalyst. The inventor surprisingly finds out that after the organic photo-sensitizer is loaded on said solid photocatalyst, the two catalysts produce a certain synergetic effect, which can greatly increase the efficiency of the photocatalytic isomerization.

DETAILED EMBODIMENTS

The invention is further described via the following examples. The examples are only illustrative, but not limiting.

1. Preparation of the Composite Catalyst

The selections and formulations of specific organic photo-sensitizers and solid photocatalysts are shown in Table 1. Detailed preparation for the composite catalyst is described as follows: an organic photo-sensitizer is dissolved in an organic solvent (e.g., ethanol) to formulate a solution having a concentration of 20 wt %, and a solid photocatalyst is dried at 100° C.; the solution containing the organic photo-sensitizer is mixed with the dried solid photocatalyst according to the weight ratio of the organic photo-sensitizer to the solid photocatalyst ranging from 0.5% to 20% with stirring for 24 hours, so that the photo-sensitizer is sufficiently adsorbed onto the surface of the solid photocatalyst and takes a sufficient interaction with hydroxyl groups on the surface or in the channel of the solid photocatalyst; thereafter, the redundant solution is filtered and the resultant solid is dried at 100° C. under vacuum for 5 hours (the vacuum level is not specifically required); thus the composite catalyst of the invention is produced. The catalyst prepared by the process of the invention is incorporated into the examples.

2. Activity Test of the Catalyst

The above catalyst particles are added to 150 ml norbornadiene according to the weight ratio of the catalysts to norbornadiene ranging from 2 to 10%. Under the conditions of nitrogen protection and magnetic stirring, the mixture is irradiated with a 400 W high pressure mercury lamp for 8 hours at 10 to 70° C. to carry out the reaction. The composition of the solution is analyzed by using a chromatographic analysis method regularly, and the yield of the target product quadricyclane is calculated. The yield at different time is described in FIG. 1, and the quadricyclane yields corresponding to individual catalysts are shown in Table 1.

In addition, under the same experimental conditions, the activities of a single organic photo-sensitizer and a single solid photocatalyst as well as a physical mixture of an organic photo-sensitizer and a solid photocatalyst are tested, and these catalysts which are not prepared by the process according to the present invention are incorporated into the comparative examples.

TABLE 1

| | Catalysts | The weight ratio of catalyst to norbornadiene | Reaction temperature | Quadricyclane yield |
|---|---|---|---|---|
| Example 1 | 0.5% diethyl Michler's Ketone/$TiO_2$ | 10% | 50° C. | 95.1% |
| Comparative Example 1 | diethyl Michler's Ketone | 10% | 50° C. | 23% |
| Comparative Example 2 | $TiO_2$ | 10% | 50° C. | 16% |
| Comparative Example 3 | A physical mixture of 0.5% diethyl Michler's Ketone and $TiO_2$ | 10% | 50° C. | 34% |
| Example 2 | 2% diethyl Michler's Ketone/Ti-MCM-41 | 8% | 10° C. | 94.3% |
| Example 3 | 5% diethyl Michler's Ketone/Ti-SBA-15 | 2% | 20° C. | 93.0% |
| Example 4 | 9% ethyl Michler's Ketone/ZnO | 4% | 30° C. | 95.4% |
| Example 5 | 12% diethyl Michler's Ketone/$WO_3$ | 7% | 40° C. | 96.0% |
| Example 6 | 15% diethyl Michler's Ketone/$Ta_2O_3$ | 5% | 60° C. | 92.2% |
| Example 7 | 20% diethyl Michler's Ketone/$SrTiO_3$ | 2% | 70° C. | 94.5% |
| Example 8 | 15% acetophenone/$TiO_2$ | 8% | 70° C. | 95.3% |
| Example 9 | 10% benzophenone/$WO_3$ | 5% | 40° C. | 93.7% |
| Example 10 | 5% Michler's Ketone/$Ta_2O_5$ | 7% | 50° C. | 90.2% |
| Example 11 | 2% tetraethyl Michler's Ketone/$SrTiO_3$ | 2% | 60° C. | 92.5% |

3. Result Analysis

As shown in FIG. 1, when the composite catalyst of the invention is used, the quadricyclane yield exhibits a linear increasing trend with time, and the yield can realize as high as 95% within 8 hours.

As seen from the comparison between Example 1 in Table 1 and Comparative Examples 1 to 3, under the same conditions, the quadricyclane yield realized by using the composite catalyst of the invention is far away higher than those realized by using a single organic photo-sensitizer, a single solid photocatalyst and a physical mixture of an organic photo-sensitizer and a solid photocatalyst. The result shows that with respect to the composite catalyst prepared by the process of the invention, the process for loading an organic photo-sensitizer on the surface or in the channel of a solid photocatalyst is absolutely not a process of uniformly dispersing one substance onto the surface of another substance, but relates to certain interactions between the two substances to produce a huge synergetic effect of 1+1>2. With respect to this phenomena, a possible reason may resides in the charge transfer between the organic photo-sensitizer and the solid photocatalyst, which promotes charge separation and increase the efficiency of the use of photo-generated charges in the isomerization, and however other reasons are not excluded, which needs further researches.

As shown in Table 1, the experimental results of Examples 2 to 11 of the invention demonstrate that when the weight ratio of the composite catalyst of the invention to norbornadiene is within a relatively low ratio range of 2% to 8%, the quadricyclane yield of greater than 90% can be realized at a temperature of 10 to 70° C. The result demonstrates that the composite catalyst of the invention has a very high activity, and thus the amount of the catalyst can be reduced.

From the experimental conditions for the catalysis activity test, the reactant norbornadiene is directly used as the medium, and thus no solvent is used in the reaction. Even under such conditions, the activity of the composite catalyst of the invention is still high, and the activities of individual catalysts in the comparative examples are poor. The result demonstrates that in the reaction the composite catalyst of the invention can get rid of dependence on the dilution solvent, which can increase the amount of the reactant to be treated by the catalyst per unit volume. Furthermore, the composite catalyst of the invention is in a solid form, which can be readily separated and recycled.

Figure 2:
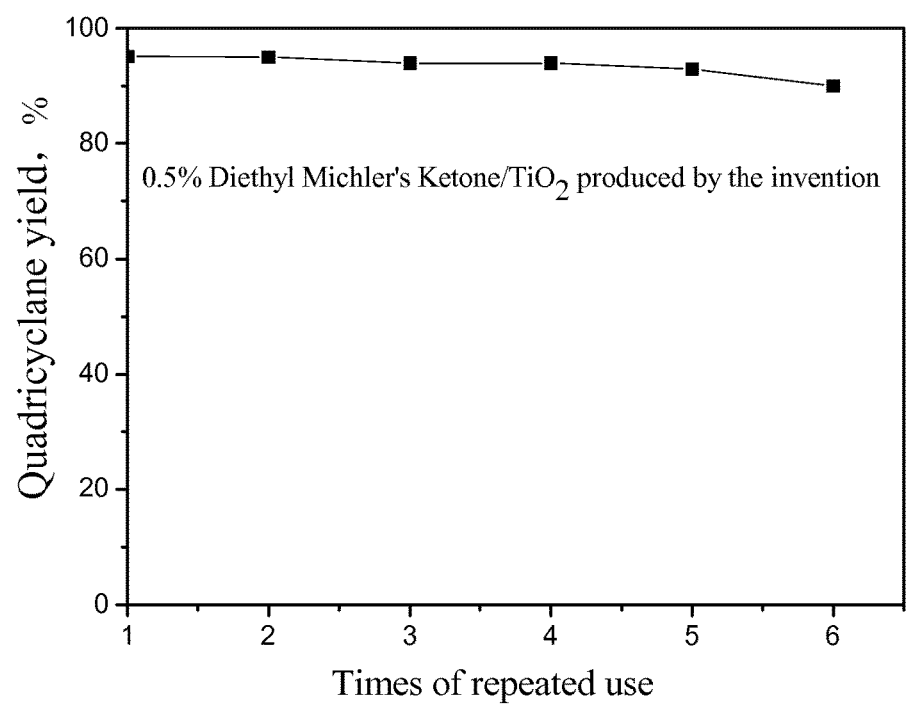
FIG. 2 is a diagram which describes the variation of the quadricyclane yield with the time in the presence of the repeatedly-used catalyst of the invention.

As seen in FIG. 2, after the composite catalyst according to the invention is recycled six times, the quadricyclane yield is still high. The result demonstrates that the activity of the composite catalyst of the invention is very stable. The possible reason may be that in the process of the invention for loading an organic photo-sensitizer onto a solid photocatalyst, the two substances are tightly bound together via chemical interactions, so that the organic photo-sensitizer is not ready to leach into the reaction medium. Of course, other reasons which are not known for the inventors and which result in the stability of the catalyst of the invention are not excluded. The stable activity of the catalyst of the invention is very advantageous for its applications in industry.

Figure 3:
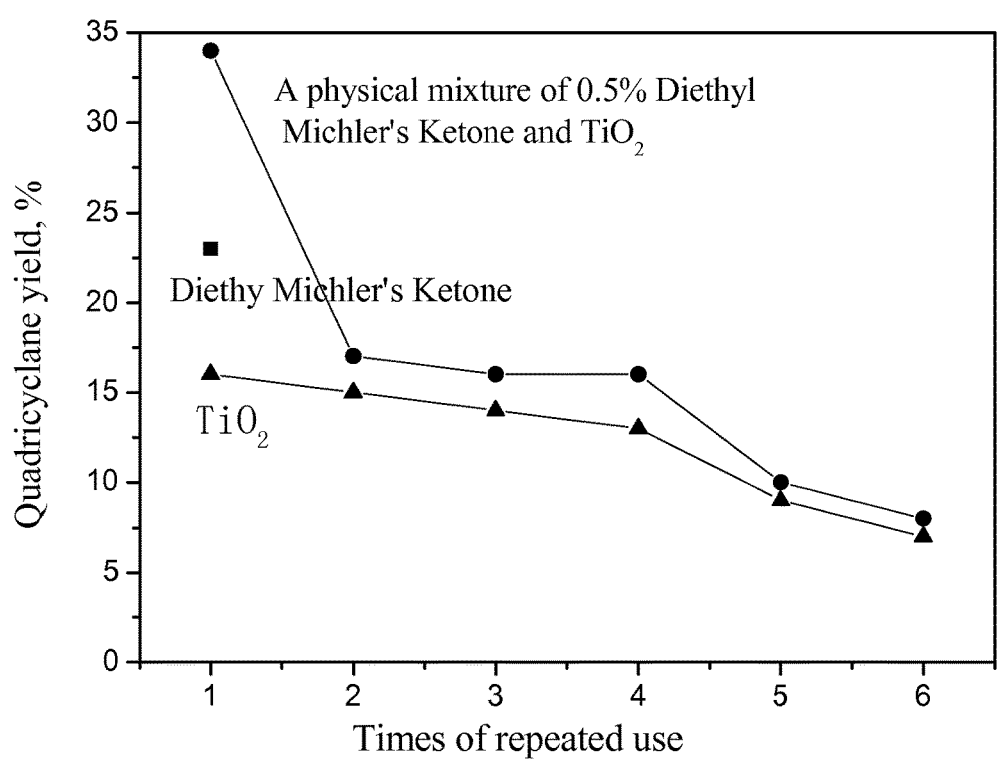
FIG. 3 is a diagram which describes the variation of the quadricyclane yield with the time in the presence of the repeatedly-used comparative catalyst.

As shown in FIG. 3, since a single photo-sensitizer is dissolved in the reaction solution, it cannot be recycled. Although a single solid photocatalyst can be recycled, its activity exhibits a decreasing trend. With respect to the physical mixture of an organic photo-sensitizer and a solid photocatalyst, after the first reaction, the quadricyclane yield is quickly decreased to a level which is comparative to that obtained by using a solid photocatalyst. The result demonstrates that the organic photo-sensitizer has been leached and lost, and the loss of the activity of the catalysts in the comparative examples is large so that they are not suitable for repeated uses in industry.

The invention claimed is:

1. A process of preparing a composite catalyst for photocatalytic isomerisation of norbornadiene to prepare quadricyclane, comprising the steps:
   (a) mixing a solution obtained by dissolving an organic photo-sensitizer in an organic solvent with a solid photocatalyst under sufficient stirring, wherein the weight ratio of the organic photo-sensitizer to the solid photocatalyst ranging from 0.5% to 20%, so that the organic photo-sensitizer is adsorbed onto a surface or a channel of the solid photocatalyst, wherein the solid photocatalyst is selected from $WO_3$, $Ta_2O_5$ or $SrTiO_3$; and the organic photo-sensitizer is selected from benzophenone, acetophenone, Michler's Ketone, tetraethyl Michler's Ketone, or diethyl Michler's Ketone; and
   (b) filtering off redundant solution and vacuum drying the solid photocatalyst which adsorbed the organic photo-sensitizer;
   wherein in the step (a), the organic photo-sensitizer is present in the solution in a concentration of 20% by weight, and the solid photocatalyst is dried at 100° C., and the stirring continues for 24 hours; and in the step (b), the vacuum drying is carried out at 100° C. for 5 hours.

* * * * *